United States Patent
Stanley, III

(10) Patent No.: US 6,680,029 B2
(45) Date of Patent: *Jan. 20, 2004

(54) INCENSE MATCH

(76) Inventor: Virgil E. Stanley, III, 5860 N. Michigan Rd., Indianapolis, IN (US) 46228

( * ) Notice: Subject to any disclaimer, the term of this patent is extended or adjusted under 35 U.S.C. 154(b) by 168 days.

This patent is subject to a terminal disclaimer.

(21) Appl. No.: 09/823,068

(22) Filed: Mar. 30, 2001

(65) Prior Publication Data

US 2001/0033811 A1 Oct. 25, 2001

Related U.S. Application Data

(63) Continuation-in-part of application No. 09/556,365, filed on Apr. 24, 2000, now Pat. No. 6,613,289.

(51) Int. Cl.⁷ .............................. C06F 3/04; A01N 25/20
(52) U.S. Cl. ........................ 422/126; 44/507; 44/511; 44/512; 44/901; 424/40
(58) Field of Search ...................... 422/5, 126; 44/507, 44/511, 901, 512; 144/60; 424/40

(56) References Cited

U.S. PATENT DOCUMENTS 4,158,549 A  *  6/1979  Martin ...................... 44/1 R X
5,865,862 A  *  2/1999  Hassan ...................... 44/507

FOREIGN PATENT DOCUMENTS

GB          882713    * 11/1961
RO          112741 B  * 12/1997

* cited by examiner

Primary Examiner—Elizabeth McKane
(74) Attorney, Agent, or Firm—Coats & Bennett, PLLC

(57) ABSTRACT

An incense device is provided and comprises an elongated incense stick that in one embodiment includes an opening. An ignition device including a head portion and a shaft portion is secured to the incense stick. In another embodiment, an ignition head is secured directly to an end portion of the incense stick.

10 Claims, 2 Drawing Sheets

INCENSE MATCH

CROSS REFERENCE TO RELATED APPLICATION

The present application is a continuation-in-part of U.S. patent application Ser. No. 09/556,365 filed on Apr. 24, 2000, now U.S. Pat. No. 6,613,289.

FIELD OF THE INVENTION

The present invention relates to an incense match and, more particularly, to a method of making such an incense match.

BACKGROUND OF THE INVENTION

Incense has been popular in Asian cultures for many centuries, and has been present in the United States for a long time as well. While the 1960s saw the use of incense skyrocket by counter-culture elements, incense has now moved into the mainstream. Incense provides not only a pleasant aroma in which to function, but also may serve as an insecticide or insect repellant. The particular combination of elements within the fumigant allows different aromas and/or different properties to be incorporated into different incense. Additionally, incense coupled with acupuncture is believed, by many, to promote healing. Additionally, a whole new field of holistic medicine, entitled Aroma Therapy, has also come to relatively recent attention by the efforts of its practitioners. Thus, it is easily seen that incense has a myriad of uses, both from a pleasure standpoint and, potentially, from a medicinal standpoint.

With the numerous uses of incense available, numerous efforts to arrive at a convenient technique for dispensing or burning incense have arisen. Incense may come in pellets, tabs, or stick form, such as a joss stick. Additionally, numerous incense-burning apparati have, likewise, been developed and patented. These apparati have given rise to specially-formed incense products which work essentially only with the particular incense-burning product. For example, U.S. Pat. No. 4,099,916 to Gardner et al. shows a particular incense-supporting apparatus with a vertical rod with a cylindrical incense fitted thereover. The incense must burn of its own accord. While the various and sundry products and incense forms do function well, there remains a need for a more universal incense-delivery technique. One such universal incense-delivery technique was suggested by U.S. Pat. No. 3,754,861 to Sadahiro, which showed a fumigant forming a body and one end of the fumigant covered by a match head. However, the '861 patent relies on the fumigant to be self-burning. While many fumigants are, in fact, self-burning, greater variety in the aroma provided by the incense is possible if the incense is not required to be self-burning. That is, more flame resistant aroma particles may be inserted into the fumigant if there is no requirement that they burn.

In short, there remains a need for a universal incense distribution product that has properties which do not require the fumigant to sustain a self-burning activity.

SUMMARY OF THE INVENTION

The shortcomings of the prior art are addressed by a hollow cylindrical incense product which is especially manufactured to fit over the shaft of a match. In particular, a conventional wooden match is preferred. Thus, the wood of the match provides the energy to char the incense as the wood combusts. This frees the incense for more aromatic elements and diminishes the need for the fumigant itself to be self-burning.

In particular, in one embodiment of the present invention, there is provided an incense device that comprises an elongated extruded incense sleeve having a central opening formed within the sleeve. A wood match having a stem portion and a head is inserted into the incense sleeve. More particularly, the stem portion is inserted into the central opening of the incense sleeve such that the head of the match remains exposed and spaced from one end of the incense sleeve.

Further, the present invention entails a method of manufacturing or forming an incense device. This entails mixing an incense composition and extruding the composition to form an elongated incense product having a central opening extending axially through the incense product. Thereafter the incense product is cut into selected lengths and then subjected to a finishing operation. Next, individual ignition devices, in one embodiment in the form of a match, are inserted into the central opening. In the case of a match, the match stem is inserted a selected distance into the central opening such that the match head that forms a part of the ignition device remains exposed and spaced from one end portion of the incense sleeve.

In another embodiment of the present invention, the incense product includes an ignition head, such as a match head, formed on the end of an incense stick. A first design includes an ignition head that is supported on a relatively short stub shaft and wherein the short stub shaft is inserted into an opening formed on the end of the incense stick. A second design provides for an ignition head, such as a match head, that is molded or fused directly to the end of the incense stick.

Other objects and advantages of the present invention will become apparent and obvious from a study of the following description and the accompanying drawings which are merely illustrative of such invention.

DETAILED DESCRIIPTION OF THE INVENTION

With further reference to the drawings, the incense device of the present invention is shown therein and indicated generally by the numeral 10.

Figure 2:
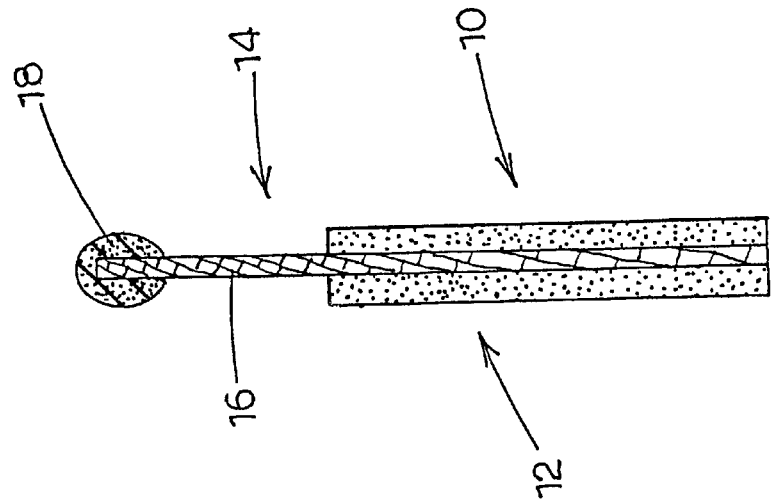
FIG. 2 is a longitudinal sectional view of the incense device of the present invention.
Figure 1:
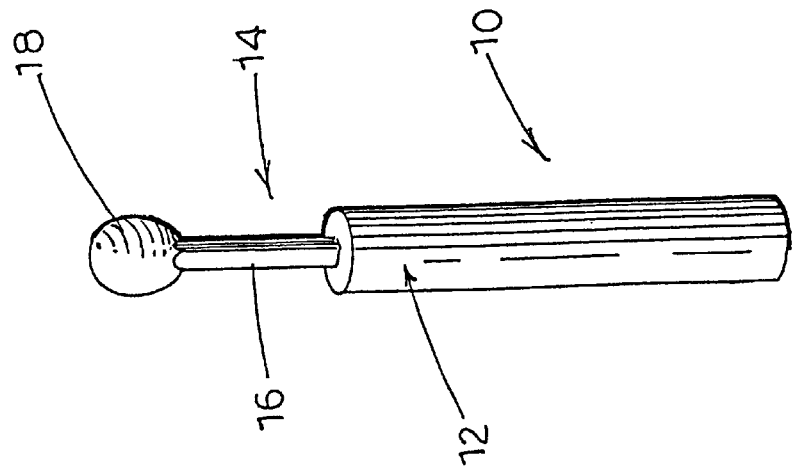
FIG. 1 is a perspective view of the incense device of the present invention.

Viewing the incense device 10 in more detail, it is seen that the same includes an incense sleeve indicated generally by the numeral 12. As will be appreciated from subsequent portions of this disclosure, the incense sleeve 12 is formed or manufactured through an extrusion process. More particularly, basic compositional components of the incense sleeve are mixed together and then extruded to form the incense sleeve. As indicated in FIG. 2, the incense sleeve 12 in the embodiment illustrated herein is generally cylindrical in shape and includes a central opening or a central bore that extends axially from one end to the other end of the incense sleeve.

After the incense sleeve 12 is manufactured, a match, indicated generally by the numeral 14, is inserted into the incense sleeve. The match 14 includes a stem portion 16 and a head or ignition portion 18. Note in the drawings where the stem portion 16 is inserted downwardly through the central opening of the incense sleeve 12 such that the head 18 of the match 14 is spaced outwardly from one end portion of the incense sleeve 12. Thus, it is appreciated that a portion of the stem 16 actually extends exposed between one end of the incense sleeve 12 and the head 18.

In the embodiment illustrated herein, the stem portion 16 of the match is wood. Therefore, by striking the match and igniting the match head 18, results in the stem portion burning. As the stem portion burns down toward the incense sleeve 12, it is appreciated that the burning of the match stem 16 will result in the incense sleeve being burned, or at least substantially heated, such that the incense sleeve begins to emit an aroma.

Figure 4:
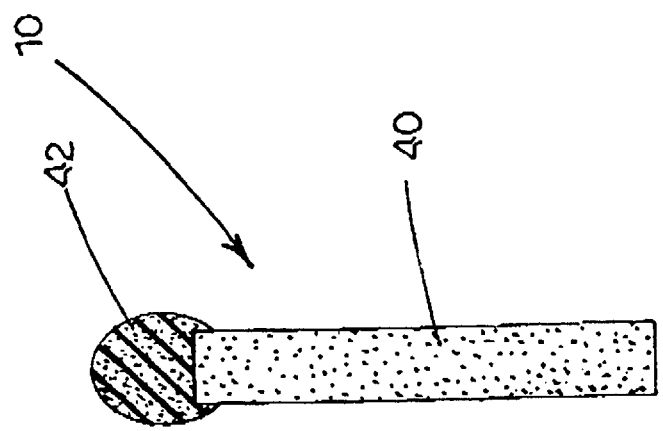
FIG. 4 is a view of another alternate design for the incense device of the present invention.
Figure 3:
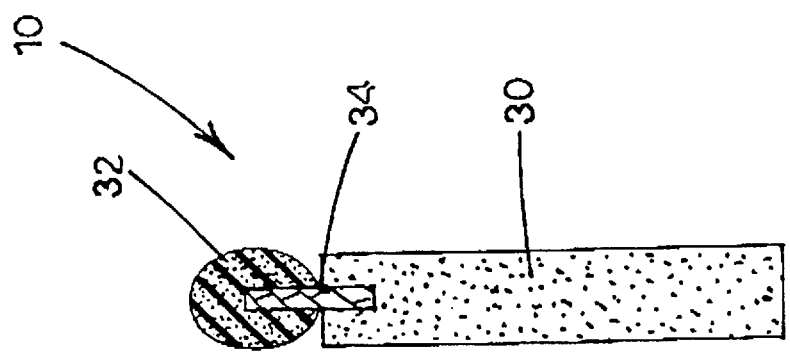
FIG. 3 is a longitudinal sectional view of an alternate embodiment of the incense device of the present invention.

Alternate designs for the incense device 10 of the present invention is shown in FIGS. 3 and 4. First, with respect to FIG. 3, there is shown therein an incense stick 30. Incense stick 30 is generally solid except for a small or short opening formed in one end. An ignition head 32 such as a match head is secured to a short stub shaft 34. The short stub shaft may be in the form of a wooden match stick or other suitable means. This short stub shaft 34 is inserted into the opening in one end of the incense stick 30. The opening in the incense stick and the diameter of the stub shaft 34 are particularly sized such that once the stub shaft 34 is inserted within the opening, a secure frictional fit is realized.

Turning to the second alternate design, shown in FIG. 4, there is shown an incense stick 40. Incense stick 40 is generally solid substantially throughout. An ignition head 42 such as a match head, is secured directly to one end of the incense stick 40. The ignition head 42 can be secured to the end of the incense stick 40 in various ways. For example, the ignition head 42 can be secured by a glue composition to the incense stick after the incense stick 40 has been produced. Alternatively, the ignition head 42 can be fused to the end of the incense stick 40 or the ignition head 42 can be secured to the incense stick through a molding or insert molding process. In any event, the point being made here is that the ignition head 42 can through appropriate securement form an integral part of the incense stick 40.

The basic components for the incense sleeve are incense powder, sawdust and incense resin. These materials in conventional fashion will be mixed in a tank with water. Thereafter, the mixed material will be directed into an extruder that will produce the incense sleeve 12.

The fragrance utilized will generally be made of an oil base. Many different aromas can be selected, including fruit and floral fragrances. For example, fragrances of apple, vanilla, cherry, bayberry, strawberry, jasmine and lavender are appropriate for incorporation into the incense stick.

Basically, the incense composition referred to above is mixed, and the mixed product is extruded into an elongated incense product. This product is cut into selected lengths. After that, the individual incense sticks, or sleeves, are subject to heat for purposes of drying. Thereafter, the top and bottom of the cut sleeves are subjected to a brushing machine so as to form smooth opposed ends about the incense sleeves.

Once a fragrance has been selected, the fragrance is typically a 100%, by weight, based oil fragrance and to that there is added alcohol and a fixative. In one particular embodiment of the present invention, the oil-based fragrance is diluted by adding the fixative and alcohol. Typically the total fragrance mixture, including the fixative and the alcohol, will comprise, by weight, approximately 30% oil-based fragrance, 10% fixative, and 60% alcohol.

Once the alcohol mixture has been prepared, the extruded incense sleeves 12 are dipped into the diluted fragrances for a selected time period. Then the incense is removed from the fragrance composition and allowed to dry.

Further, the composition utilized to manufacture the incense stick can be provided with insecticidal ingredients. During the burning of the incense, the fragrance emits an aroma that is effective to either kill insects or to discourage insects from inhabiting the immediate area around the burning incense.

Therefore, from the foregoing discussion and specification, it is appreciated that the incense device of the present invention has many advantages over incense sticks of the prior art. By incorporating a match structure into the incense, it follows that the stem of the match forms a structural support within the incense itself. Further, because the stem of the match burns in response to the match being ignited, it follows that the match stem itself provides energy, in the form of heat, for activating or burning the incense sleeve.

The present invention may, of course, be carried out in other specific ways than those herein set forth without departing from the spirit and the essential characteristics of the invention. The present embodiments are, therefore, to be construed in all aspects as illustrative and not restrictive, and all changes coming within the meaning and equivalency range of the appended claims are intended to be embraced therein.

What is claimed is:

1. An incense device comprising: an elongated incense stick having an opening formed therein; the incense stick comprising an incense powder, sawdust and a resin; and an ignition device having a head and a shaft extending from the head and wherein the shaft is inserted and held within the opening of the incense stick and wherein the head is exposed and projects from the end of the incense stick; and wherein the shaft projects from the incense stick such that the ignition head is spaced outwardly from the end of the incense stick and wherein a portion of the shaft extending between the end of the incense stick and the head is exposed.

2. The incense device of claim 1 wherein the opening formed in the incense stick is an elongated central opening that extends substantially through the incense stick.

3. The incense stick of claim 1 wherein the incense stick is extruded to form an incense sleeve that assumes a generally cylindrical configuration and wherein the opening formed therein extends axially substantially through the incense sleeve.

4. The incense device of claim 1 manufactured by the process of extruding an incense composition to form an elongated incense product; cutting the incense product into selected lengths to form incense sticks; and then inserting a match into each incense sleeve such that the head of the match is left exposed.

5. The incense device of claim 4 wherein the incense product, after extrusion, is subjected to heat.

6. The incense device of claim 1 wherein the incense stick is in the form of an elongated sleeve having a central opening extending substantially through the incense stick, and wherein the shaft of the ignition device extends into and through the central opening of the incense stick and wherein the ignition head is disposed exteriorly of the ignition stick.

7. An incense stick comprising an incense stick having a pair of opposed ends and an ignition head secured to one end of the incense stick without a supporting structure extending from the ignition head into the body of the incense stick; and wherein the incense stick comprises incense powder, sawdust and a resin.

8. The incense stick of claim 7 wherein the ignition head is secured to the body of the incense stick by a process taken from the group including: gluing, molding, insert molding, and fusing.

9. A method of forming an incense device comprising: forming an elongated incense stick from an incense composition comprising incense powder, sawdust and a resin; forming an opening in the incense stick; and inserting a lighting device having a stem portion and an ignition head within the incense stick.

10. The method of claim 9 wherein forming the incense stick includes mixing the incense composition together and extruding the incense composition to form an elongated incense product having a central opening formed therein, thereafter cutting the incense product into selected lengths, after which the lighting device is inserted into each cut incense stick.

* * * * *